United States Patent [19]

Alten

[11] Patent Number: 4,852,554

[45] Date of Patent: Aug. 1, 1989

[54] RECONSTRUCTIVE ORTHOPEDIC DEVICES FOR CADAVERS

[76] Inventor: Michael N. Alten, 248 Sunset Rd., Avon Lake, Ohio 44012

[21] Appl. No.: 255,615

[22] Filed: Oct. 11, 1988

[51] Int. Cl.⁴ .............................................. A61F 5/00
[52] U.S. Cl. ....................................... 128/68; 623/27; 623/38; 623/57; 623/59
[58] Field of Search ...................... 27/21.1, 1; 623/27, 623/38, 57, 59; 446/320; 223/66; 128/68

[56] References Cited

U.S. PATENT DOCUMENTS

| | | | |
|---|---|---|---|
| 2,696,817 | 4/1952 | Prevo | 623/59 |
| 3,319,846 | 5/1967 | Wolf | 446/320 |
| 4,274,165 | 6/1981 | Ivko et al. | 623/57 |
| 4,676,800 | 6/1987 | Chen | 623/38 |

*Primary Examiner*—Paul T. Sewell
*Assistant Examiner*—Huong Q. Pham
*Attorney, Agent, or Firm*—Gustalo Nunez

[57] ABSTRACT

Reconstructive orthopedic prosthesis devices for cadavers comprised of plastic tubing, elbows and fasteners, for use by undertakers and morticians. The devices are used in cadavers whose bones have been harvested for bone banks, in order to give the cadaver a normal appearance.

2 Claims, 3 Drawing Sheets

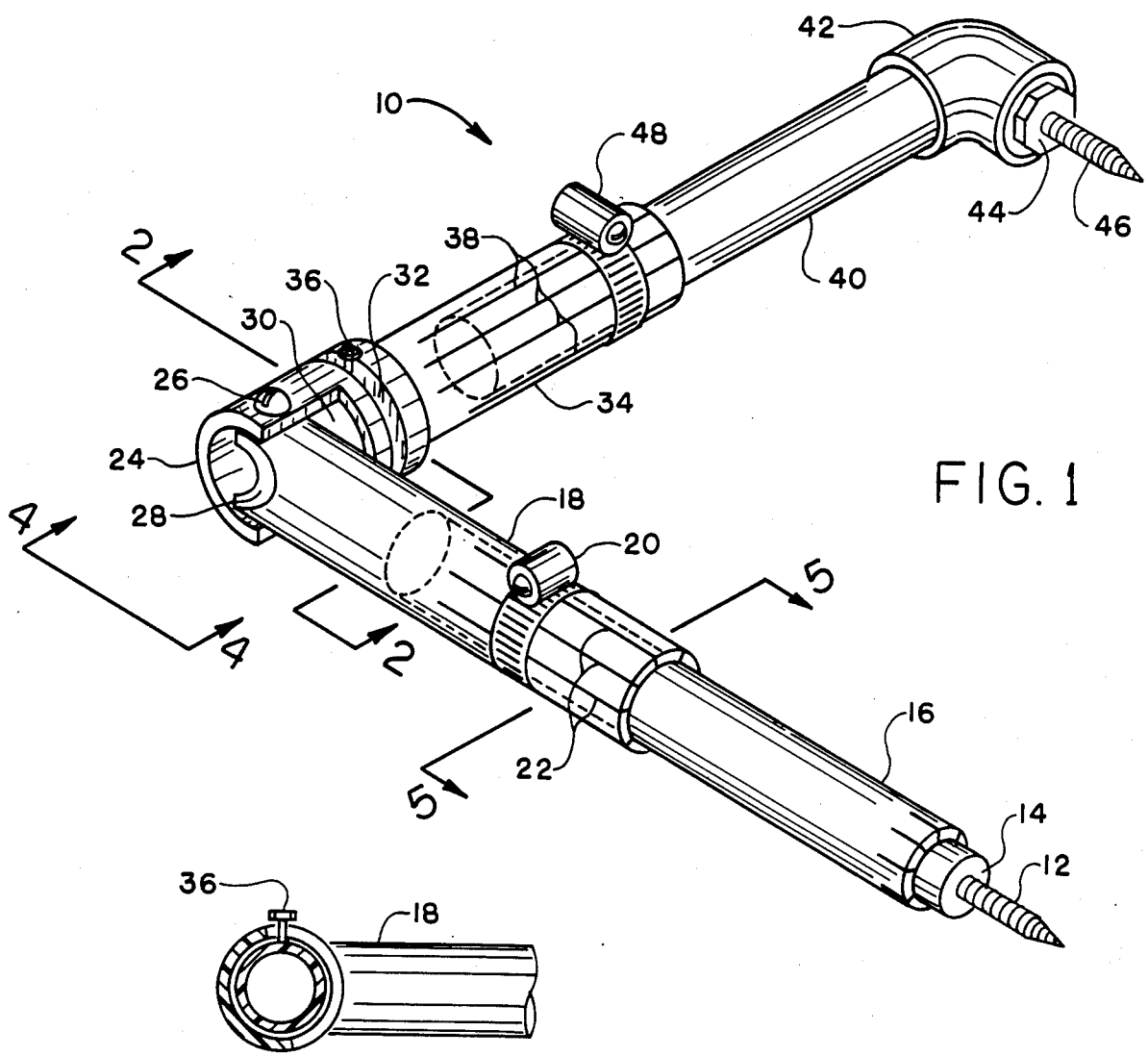
FIG. 1
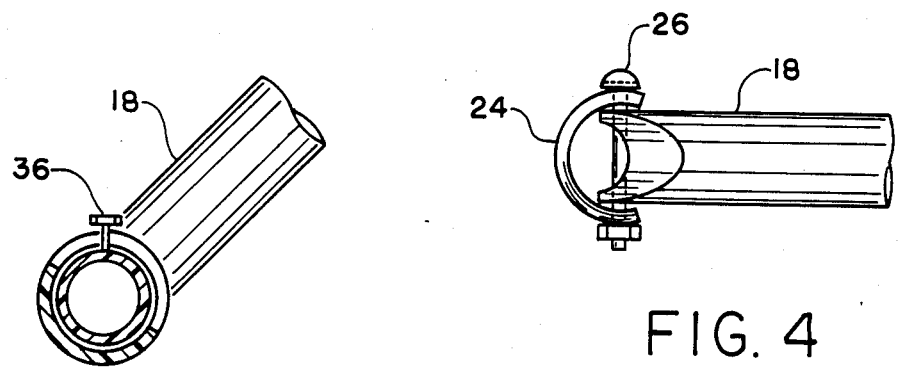
FIG. 2
FIG. 3
FIG. 4

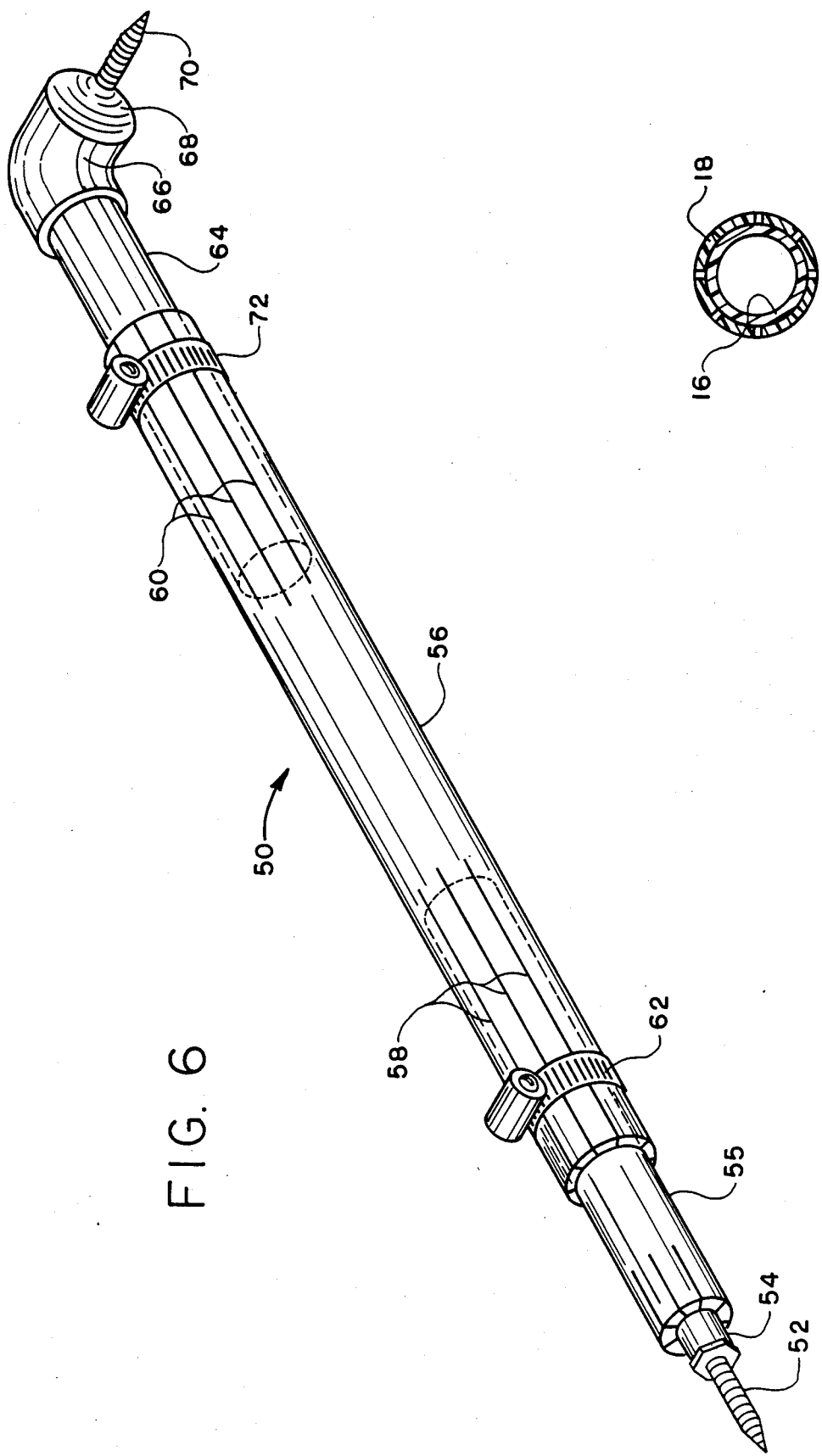

RECONSTRUCTIVE ORTHOPEDIC DEVICES FOR CADAVERS

FIELD OF THE INVENTION

This invention relates to orthopedic prosthesis devices for cadavers to compensate for missing bones or to replace bones which have been removed from the cadaver for human transplant purposes.

BACKGROUND OF THE INVENTION

In this day of modern surgery it is not at all uncommon to hear that an individual has undergone a liver transplant, lung transplant, heart transplant, skin transplant and on and on. Well, for quite some time, bones have also been transplanted. These bones, generally speaking, the long bones such as the femur, tibia, humerus, ulna, etc., are removed from those cadavers that have been identified as donors for deposit with a bone bank for use in a transplant. This leaves the cadaver with an abnormal appearance. This is not good, for the relatives and friends of the deceased do not want to see a disfigured body or a body with an abnormal appearance. They want the body to appear as normal as possible. Although applicant is not aware of any prior art, it is known that morticians have been using broom sticks as prosthesis devices. However, it is also well known that these devices are clumsy to work with and difficult to implant into a body. Applicant's invention is rather simple to make and very easy to implant.

DESCRIPTION OF THE PRIOR ART

The only art known which relates to the field of the invention is U.S. Pat. No. 3,121,934 which is directed to a postmortem chest plate for cadavers. The invention is used on cadavers that have undergone postmortem examinations. Postmortem examinations require that the chest plate be removed from the cadaver. In order to give the cadaver a normal appearance for showing, the chest plate is used on the cadaver which results in the cadaver having a normal appearance.

SUMMARY OF THE INVENTION

It is not at all uncommon to hear the expressions eye bank, skin bank, bone bank, etc. In this day of modern medicine heart transplants, eye transplants, bone transplants, etc., are all very common. Many states have laws whereby an individual can identify himself or herself as a donor of body parts at the time of death. This is commonly done by signing a donor pledge on the back of a driver's license.

When bones are removed from the body, there is no internal structure to support the skin. Consequently, the skin will sag at those areas where the bones are removed. The instant invention enhances the replacement of the removed bones and also permits the restoration of the body to a normal appearance. The invention consists of elongated cylindrical tubes telescopically connected to other cylindrical tubes. The connections are such that they are adjustable in order that the limb be placed in a desired position.

DESCRIPTION OF THE DRAWINGS

FIG. 1 is an elevation view partially in cross-section of one embodiment of the invention used to replace the humerous and ulna of the human body.

FIG. 2 is a view taken along line 2—2 of FIG. 1.

FIG. 3 is a view of FIG. 2 illustrating the rotatability of the extending lower arm piece.

FIG. 4 is a view taken along line 4—4 of FIG. 1.

FIG. 5 is a view taken along line 5—5 of FIG. 1.

FIG. 6 is an elevation view, partially in cross-section of a second embodiment of the invention used to replace the femur and tibia of the human body.

DETAILED DESCRIPTION OF THE PREFERRED EMBODIMENT

Figure 7:
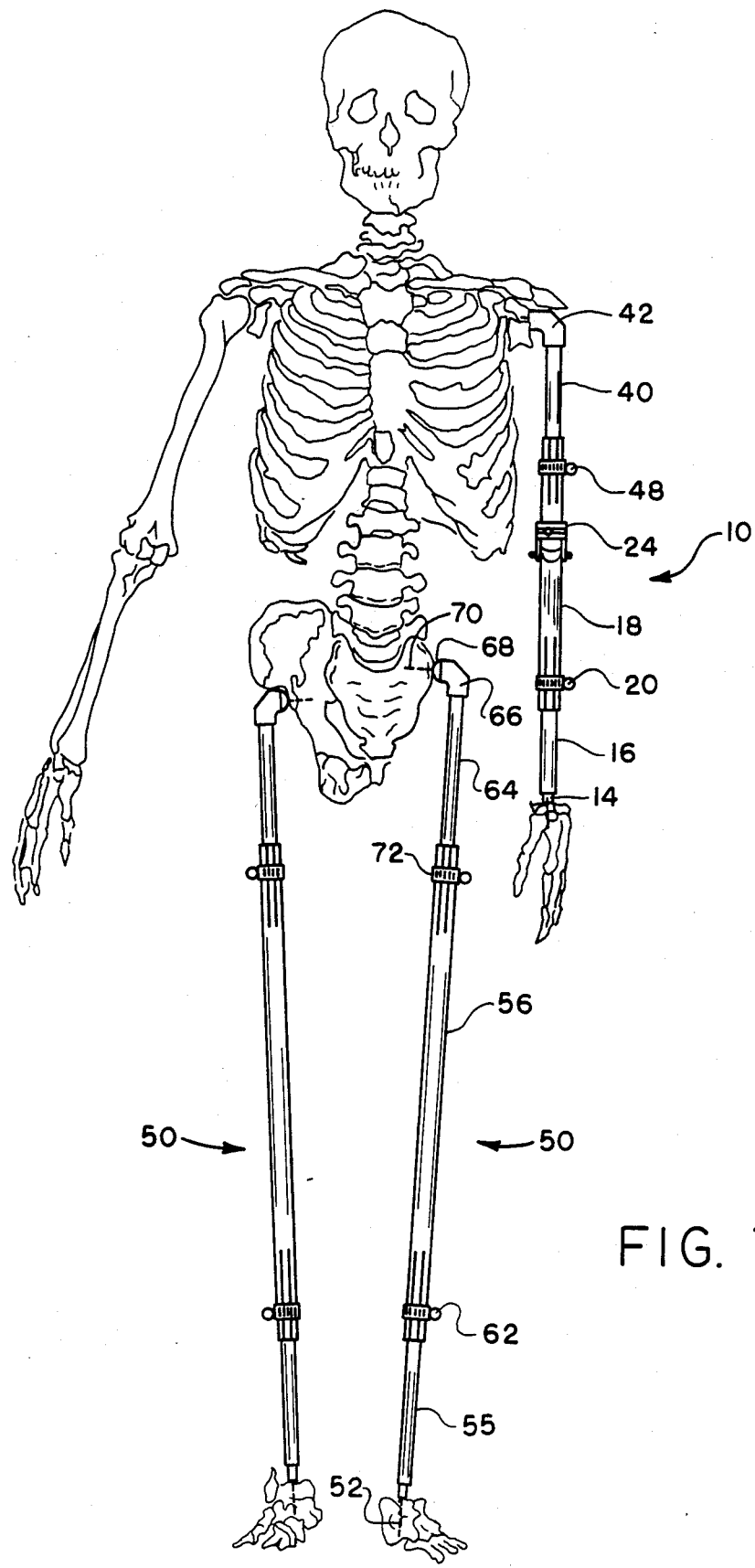
FIG. 7 is an overall plan view of the invention used with the human skeletal system.

Describing now the preferred embodiment of the invention, it is to be understood that the invention is being described as being used to replace the long bones, e.g. of humerous, ulna, femur and tibia, of the human body. However, the invention can also be used for small bone replacement. Referring now to FIG. 1, there is illustrated a view of one embodiment of the invention which is used to replace the long bones in the human arm, and which is generally referred to as the arm member 10. The arm member 10 includes a screw 12 which is attached to a plug member 14. Plug member 14 is adapted to be received by an elongated cylindrical member 16 and which is held in place by conventional means such as an adhesive. Cylindrical member 16 is telescopically inserted in a second cylindrical member 18 and is held in place with respect to cylindrical member 16 by conventional clamp means 20. The second cylindrical member 18 includes a plurality of elongated slits 22, all parallel to the longitudinal axis of the second cylindrical member 18. The slits 22 facilitate the placement of the cylindrical member 16 within the opening defined by the second cylindrical member 18.

The second cylindrical member 18 is pivotally connected to an elbow member 24 by conventional screw means 26. The terminating end of the second cylindrical member 18, at the end connected to the elbow member 24, is cut at an oblique angle at 28, see FIGS. 1 and 4. The oblique cut is parallel to the screw member 26, and the cut is also made on the other side of the cylindrical member 18. The cut 28 facilitates the movement of member 18 about the pivot point defined by the screw 26. Elbow member 24 generally resembles an elongated cylinder with a portion 30 cut away at one end thereof, said cutaway portion 30 providing an opening in which the second cylindrical member 18 can be rotated. The elbow member 24 is also provided with a slit 32 which is transverse to the longitudinal axis of the elbow member 24. A third cylindrical member 34 is adapted to be received by the elbow member 24 at the terminating end adjacent to the slit 32. The third cylindrical member 34 is held in place with respect to elbow member 24 by a screw member 36 which is inserted through the slit 32 and screwed into the third cylindrical member 34. The third cylindrical member 34 is rotatably adjustable when inserted into the elbow member 24 until the desired position is achieved, at which time the screw member 36 is tightened thereby preventing any movement between the third cylindrical member 34 and elbow member 24. The third cylindrical member 34 is further provided with longitudinal slits 38 which facilitate the reception of a fourth cylindrical member 40. The other end of the fourth cylindrical member 40 is inserted into a curved cylindrical member 42 which represents the humerous head in human anatomical terms. The curved member 42 generally resembles an elbow and terminates at the end away from the fourth cylindrical member 40 in a plug 44 and screw 46.

In use, the arm system disclosed above and shown in FIGS. 1 through 5, consists of an upper arm portion which includes the cylindrical members 34 and 40 and the lower arm portion which includes cylindrical members 16 and 18. The upper arm and lower arm portions are joined by an elbow member 24 which allows both a flexing motion at 26 and a rotational motion at 36. The lower arm portion is attached to the wrist by means of the screw 12 which in this instance can be a self-tapping screw. The upper arm portion is attached to the shoulder by means of a self-tapping screw 46.

The upper arm portion can be set to the length desired simply by sliding cylindrical member 40 into cylindrical member 34. Upon setting the desired length, the clamp 48 is tightened, thereby locking cylindrical members 34 and 40 in place with respect to each other.

Similarly, the lower arm portion can be adjusted to the desired length simply by moving the cylindrical member 16 in or out of cylindrical member 18, depending on the length required by the arm on the cadaver.

Referring now to FIG. 6, a prosthesis appliance used to replace the leg bones is shown generally at 50. Starting at the left portion of FIG. 6 a screw, self-tapping in this instance, is shown at 52 attached to an extending cylindrical plug member 54. The attachment may be made by conventional thread means or screw means.

The plug member 54 is telescopically connected to a first elongated cylindrical member 55. The end of the first elongated cylindrical member 55 away from said plug member 54 is telescopically inserted into a second elongated cylindrical member 56 which includes a plurality of longitudinal slits 58 and 60 at each end thereof. Also located at the end where the slits 58 are positioned is a clamp member 62. At the other end of the cylindrical member 50, where the slits 60 are located, is a cylindrical member 64 which is adapted to be telescopically received by the cylindrical member 56. The end of cylindrical member 64 is inserted into an elbow member 66 which then terminates in a plug member 68. Screw means 70 are attached to the plug member 68. Also, at the end of cylindrical member 56 where the slits 60 are located, is a clamp member 72.

Generally speaking, as can be seen, the leg portion is made in three pieces. The upper portion is screwed to the hip by means of screw 70. The lower portion is secured to the articulation of the foot by means of screw 52. The proper length is obtained simply by sliding members 54 and/or 64 up or down. Once the desired length is had, the clamps 62 and 72 are tightened.

FIG. 7 illustrates the skeletal system of the human body with arm and leg prostheses in place.

It has been found that plastic pipe makes a very fine material in which to practice the invention.

The prosthesis devices described herein are replacements for bones removed from a deceased donor body. By no means are these implied to be used in living human beings.

Materials that have been found to be suitable for use in this manner are plastic type materials, e.g. plastic pipe.

Accordingly, while the invention has been described with particular reference to specific embodiments thereof in the interest of complete definiteness it will be understood that it may be embodied in a variety of forms diverse from those shown and described without departing from the spirit and scope of the invention as defined by the following claims.

What I claim is:

1. A reconstructive prosthesis device adapted to be used with cadavers as replacement bones comprising:

a first elongated member having first and second terminating ends, said first terminating end terminating in a first plug member having a fastening member integral thereto, a second elongated member, having first and second terminating ends, wherein said first terminating end is adapted to telescopically receive the second terminating end of said first elongated member, means for holding said first and second elongated members in fixed relationship with respect to each other, said second terminating end of said second elongated member being pivotally connected to an elbow member having a defined pivot point, a third elongated member having first and second terminating ends, wherein said first terminating end is rotatably connected to said elbow member, and a fourth elongated member having first and second terminating ends, said first terminating end telescopically connected to said second terminating end of said third member, said second terminating end of said fourth elongated member affixed to a second plug member having fastening means thereon.

2. A reconstructive prosthesis device for use as replacement bones for cadavers, thereby giving the cadaver a normal appearance, comprising:

a first elongated cylindrical member having a first and second terminating ends, said first and terminating in a first plug member having a first fastening member integral thereto, a second elongated cylindrical member, having first and second terminating ends, where said first terminating end is adapted to telescopically receive the second terminating end of said first cylindrical member, means for holding said first and second cylindrical means in fixed relationship with respect to each other, said second terminating end of said second elongated cylindrical member being pivotally connected to an elbow member having a defined pivot point, said pivot point being transverse to the plane of rotation of said second elongated cylindrical member, a third elongated cylindrical member having first and second terminating ends, wherein said first terminating end is rotatably connected to said elbow member, and including means to affix said third elongated member to said elbow member, and a fourth elongated cylindrical member having first and second terminating ends, wherein said first terminating end is telescopically connected to said second terminating end of said third elongated cylindrical member, said second terminating end of said fourth elongated cylindrical member affixed to a plug member having a second fastening member thereon, said first fastening member connected to a bony mass such as a shoulder in the cadaver, and said second fastening member connected to a bony mass such as a foot.

* * * * *